United States Patent
Wright et al.

(10) Patent No.: US 8,722,087 B2
(45) Date of Patent: *May 13, 2014

(54) TITRATION DOSING REGIMEN FOR CONTROLLED RELEASE TRAMADOL

(75) Inventors: Curtis Wright, Norwalk, CT (US); Robert Colucci, Newtown, CT (US); Raymond Sanchez, Killingworth, CT (US)

(73) Assignee: Purdue Pharma L.P., Stamford, CT (US)

( * ) Notice: Subject to any disclaimer, the term of this patent is extended or adjusted under 35 U.S.C. 154(b) by 395 days.

This patent is subject to a terminal disclaimer.

(21) Appl. No.: 12/193,329

(22) Filed: Aug. 18, 2008

(65) Prior Publication Data
US 2008/0319085 A1 Dec. 25, 2008

Related U.S. Application Data

(62) Division of application No. 10/800,254, filed on Mar. 10, 2004, now Pat. No. 7,413,749.

(60) Provisional application No. 60/453,848, filed on Mar. 11, 2003.

(51) Int. Cl.
*A61K 9/22* (2006.01)
*A61K 9/00* (2006.01)

(52) U.S. Cl.
USPC ......................................... 424/468; 424/400

(58) Field of Classification Search
USPC .................................................. 424/400, 468
See application file for complete search history.

(56) References Cited

U.S. PATENT DOCUMENTS

| | | | |
|---|---|---|---|
| 5,672,360 | A | 9/1997 | Sackler et al. |
| 6,254,887 | B1 | 7/2001 | Miller et al. |
| 6,306,438 | B1 | 10/2001 | Oshlack et al. |
| 6,326,027 | B1 | 12/2001 | Miller et al. |
| 6,339,105 | B1 | 1/2002 | Kamin et al. |
| 6,387,956 | B1 | 5/2002 | Shapira et al. |
| 7,074,430 | B2 | 7/2006 | Miller et al. |
| 2004/0224949 | A1 | 11/2004 | Pawan et al. |
| 2006/0099249 | A1 | 5/2006 | Seth et al. |
| 2008/0069888 | A1 | 3/2008 | Seth et al. |

FOREIGN PATENT DOCUMENTS

| | | |
|---|---|---|
| WO | 00/25769 | 5/2000 |
| WO | 03/072025 | 9/2003 |
| WO | 2004/037222 | 5/2004 |
| WO | WO 2004/080447 | 9/2004 |

OTHER PUBLICATIONS

Adler, L "A comparison of once-daily tramadol with normal release tramadol in the treatment of pain in osteoarthritis" *J. Rheumatol.* 29(10): 2196-2199 (2002).
Babul, N. et al., "Efficacy and safety of extended-release once-daily tramadol in chronic pain: A randomized, 12-week clinical trial in osteoarthritis of the knee" *J. Pain and Symptom Management* 28(1): 59-71 (2004).
Barkin, RL "Alternative dosing for tramadol aids effectiveness" *Formulary* 30(9): 542-543 (1995).
Bodalia, B et al., "A comparison of the pharmacokinetics, clinical efficacy, and tolerability of once-daily tramadol tablets with normal release tramadol capsules" *J. Pain and Symptom Management* 25(2): 142-149 (2003).
Boreau F. et al., "Tramadol in post-herpetic neuralgia: a randomized, double-blind, placebo-controlled trial" *Pain* 104(1-2): 323-331 (Jul. 2003).
Burgi, W et al., *Schweiz. Med. Wschr.* 104(48): 1720-1724 (1974). (English abstr.).
Fleischmann, R et al., "Tramadol for the treatment of joint pain associated with osteoarthritis: a randomized, double-blind, placebo-controlled trial" *Current Therapeutic Res.* 62(2): 113-128 (2001).
Petrone, D et al., "Slowing the titration rate of tramadol HCI reduces the incidence of discontinuation due to nausea and/or vomiting: a double-blind, randomized trial" *J. Clinical Pharmacy and Therapeutics* 24: 115-123 (1999).
Price, PM et al., "Tramadol in the treatment of special pain: a short report based on the results of a survey of 50 patients" *Br. J. Med. Economics* 9(1): 17-20 (1995).
Ruoff, GE "Slowing the initial titration rate of tramadol improves tolerability" *Pharmacotherapy* 19(1): 88-93 (1999).
Shimp, LA "Safety issues in the pharmacological management of chronic pain in the elderly" *Pharmacotherapy* 18(6): 1313-1322 (1998).
"Defendants' Post-Trial Brief" dated May 22, 2009, corrected Jun. 17, 2009, in: C.A. No. 07-255 (KAJ) Consolidated; United States District Court for the District of Delaware.
"Plaintiffs' Reply to Defendants' Proposed Findings of Fact and Conclusions of Law" dated Jun. 15, 2009, in: C.A. No. 07-255 (KAJ) Consolidated; United States District Court for the District of Delaware.
"Defendants' Post-Trial Reply Brief" dated Jun. 15, 2009, in: C.A. No. 07-255 (KAJ) Consolidated; United States District Court for the District of Delaware.
"Plaintiffs' Corrected Proposed Findings of Fact and Conclusions of Law After Trial" filed May 22, 2009, corrected Jun. 15, 2009, in: C.A. No. 07-255 (KAJ) Consolidated; United States District Court for the District of Delaware.
"Defendants' Proposed Findings of Fact and Conclusions of Law" corrected Jun. 17, 2009, in: C.A. No. 07-255 (KAJ) Consolidated; United States District Court for the District of Delaware.
Decision dated Aug. 13, 2009 and mailed Aug. 18, 2009, granting request for ex parte Reexamination of U.S. Patent 7,413,749.
Replacement request for ex parte Reexamination of U.S. Patent 7,413,749 filed Jul. 7, 2009.
Statement from patent holder dated Aug. 22, 2011, in Opposition to EP 1601350.

(Continued)

*Primary Examiner* — Maryam Monshipouri
(74) *Attorney, Agent, or Firm* — Ostrolenk Faber LLP

(57) ABSTRACT

A titration dosing regimen for the administration of controlled release tramadol analgesic to patients. The titration dosing regimen provides a significant reduction in the occurrence of adverse effects from the introduction of controlled released tramadol dosing, thus increasing patient compliance and medication tolerability.

20 Claims, No Drawings

(56) References Cited

OTHER PUBLICATIONS

Notice of Appeal by patent holder in Opposition to EP 1601350 dated Jun. 20, 2011.
Minutes of Oral Hearing in Opposition to EP 1601350 dated Apr. 12, 2011.
Decision in Opposition to EP 1601350 dated Apr. 12, 2011.
Grounds for decision in Opposition to EP 1601350 dated Apr. 12, 2011.
Amendment by patent holder patent holder dated Feb. 22, 2011 in Opposition to EP 1601350.
Cancer Pain Relief. 2002, (WHO Guidelines) A guide to opioid availability, 2nd Ed. ISBN: 92 4 154482 1. (NLM Classifaction: QZ 200).
Rote Liste 2002 Second edition, Published by Edito Cantor Ceasar, Editior: Aulendorf, DE.
Communication in EP Application 04 719 852.8 Dated Feb. 8, 2007.
Entry from the 2001 Physician's Desk Reference for MS Contin.
Villalba, Lourdas, (2004) Clinical Review: Tramadol Extended Release. NDA 21-692, Review completion date: Oct. 29, 2004.
Delaware Civil Action: 07-255-KAJ *Purdue Pharma Products et al.* v. *Par Pharmaceutical Inc. et al.* Findings of fact and conclusions of law. Aug. 14, 2009.
Patent Holder Reply in Opposition to EP 1601350 dated Apr. 14, 2011.
Declaration of Raymond Sanchez, M.D. Under 37 C.F.R. § 1.131 in U.S. Appl. No. 90/010,576, Executed Jun. 3, 2010.
Declaration of Curtis Wright IV, M.D., M.P.H Under 37 C.F.R. § 1.131 in U.S. Appl. No. 90/010,576, Executed Jun. 18, 2010.
Declaration of Dr. Robert Colucci 37 C.F.R. § 1.131 in U.S. Appl. No. 90/010,576, Executed Jun. 11, 2010.
Declaration of Dr. Robert Colucci 37 C.F.R. § 1.131 in U.S. Appl. No. 90/010,576, Executed Apr. 27, 2010.
A Matter Maintenance Memo from the law firm of Pennie & Edmonds LLP, dated May 2, 2002, opening the prosecution file for the Titration Dosing Regimen for Controlled-Release Tramadol priority application.
A letter, with attached copies of redacted internal emails, from Phil Strassburger of Purdue to James Markey of Pennie & Edmonds, dated May 2, 2002, enclosing, inter-company documents regarding tramadol, including the Clinical Study Report.
An email, with redacted attachments, from Dr. Colucci to his assistant, Ms. Peterson, which was then mailed to James Markey, dated Jun. 27, 2002, enclosing data from Purdue clinical studies conducted regarding tramadol, Attachments: 120 Day Safety Update for THCR, Tramadol HCI CR (THCR) Tablets, formulation and process, and email from Levy, Seth to Huang, Larry, cc: Oshlack, Ben, RE: Dosage of Tramadol Used in the [redacted] MD Protocol, dated Jun. 6, 2002.
A letter from James Markey to Dr. Colucci, dated Sep. 25, 2002, enclosing a preliminary patent application directed to Titration Dosing Regimen for Controlled-Release Tramadol.
A letter from James Markey to Dr. Colucci, dated Nov. 13, 2002, enclosing a revised draft patent application directed to Titration Dosing Regimen for Controlled-Release Tramadol.
A letter from James Markey to Mr. Benjamin Oshlack of Purdue, dated Dec. 6, 2002, enclosing a revised draft patent application directed to Titration Dosing Regimen for Controlled-Release Tramadol.
A communication from James Markey to Dr. Curtis Wright of Purdue, a coinventor on the '749 patent, and Dr. Colucci, dated Dec. 18, 2002, enclosing a revised draft patent application directed to Titration Dosing Regimen for Controlled-Release Tramadol.
A Fedex letter from James Markey to Dr. Raymond Sanchez, a coinventor on the 749 patent, dated Jan. 24, 2003, enclosing a revised draft patent application directed to Titration Dosing Regimen for Controlled-Release Tramadol and the Clinical Study Report; the letter also set forth a confidentiality agreement signed by Dr. Sanchez.
A communication from Dr. Sanchez to James Markey, dated Feb. 21, 2003, enclosing the revised draft patent application directed to Titration Dosing Regimen for Controlled-Release Tramadol with comments noted thereon.
A communication from Dr. Sanchez to James Markey, dated Feb. 26, 2003, enclosing a signed declaration related to the patent application directed to Titration Dosing Regimen for Controlled-Release Tramadol.
A letter from James Markey to Dr. Colucci dated Feb. 27, 2003, enclosing an original of the patent application directed to Titration Dosing Regimen for Controlled-Release Tramaclol, as well as a declaration prepared for the signature of Dr. Wright and Dr Colucci (already signed by Dr. Sanchez).
A letter from Sharon Kenney, assistant to Dr. Colucci, to James Markey, dated Mar. 7, 2003, enclosing the patent application directed to Titration Dosing Regimen for Controlled-Release Tramadol and the declaration signed by Dr. Wright and Dr. Colucci.
PubMed Health Tramadol internet site: http://www.ncbi.nlm.gov/pubmedhealth/PMH0000960 Retrieved Sep. 20, 2010, pp. 1-5.
Barkin RL, 2008 Extended-release Tramadol (ULTRAM ER): a pharmacotherapeutic, pharmacokinetic, and pharmacodynamic focus on effectiveness and safety in patients with chronic/persistent pain Am J Ther. 15(2):157-66.
Pascual ML et al., 2007, Open-label study of the safety and effectiveness of long-term therapy with extended-release tramadol in the management of chronic nonmalignant pain, Curr Med Res Opin. 23(10):2531-42.
Examiner's Answer to Appeal Brief in Ex Parte Reexamination Proceeding regarding parent U.S. Patent 7,413,749 mailed Jun. 20, 2012.
Reply Brief Filed and Request for Oral Hearing in Ex Parte Reexamination Proceeding regarding parent U.S. Patent 7,413,749 submitted Aug. 20, 2012.
Reply Brief Noted in Ex Parte Reexamination Proceeding regarding parent U.S. Patent 7,413,749 mailed Aug. 27, 2012.
Appeal Docketing Notice in Ex Parte Reexamination Proceeding regarding parent U.S. Patent 7,413,749 mailed Sep. 19, 2012.
Opposition filed by Biovail in the European Patent Office against related European Patent EP 1601350 on Oct. 10, 2009.
BW Healthwire article entitled "Biovail Reports Second Positive Phase III Clinical Result for Tramadol Extended Release Formulation" (dated Jan. 14, 2002).
Business Wire Report entitled "Biovail presents Tramadol results at American College of Rheumatology" dated Oct. 28, 2002.
Medscape Medical News article entitled "Extended-Release Tramadol Reduces Symptoms in Chronic Knee Pain" dated Oct. 27, 2002.
Medscape Medical News article entitled "Clinical Advances in Osteoarthritis" dated Nov. 25, 2992.
Sista, et al., "Steady State Dose Proportionality of a Novel Formulation of Tramadol HCI Extended Release Tablets" *AAPS Pharmsci.* vol. 5(S1), Abstract 1803 (2003).
Poster presented at the AAPS Annual Meeting between Oct. 26 and 30, 2003, entitled "The Pharmacokinetics of Novel Once Daily Tramadol Hydrochloride Extended Release Tablets in Health Subjects".
Lai et al., "The Pharmacokinetics of Novel Once Daily Tramadol Hydrochloride Extended Release Tablets in Healthy Subjects" *AAPS Pharmsci.* vol. 5(S1), Abstract 1814, (2003).
Declaration of Dr. Okponanabrofa Eradiri of Biovail Corporation in support of BW Healthwire article entitled "Biovail Reports Second Positive Phase III Clinical Result for Tramadol Extended Release Formulation" (dated Oct. 12, 2009).
Declaration of Dr. Okponanabrofa Eradiri of Biovail Corporation in support of Poster presented at 66th Annual Scientific Meeting of the American College of Rheumatology on Oct. 26, 2002 entitled "A double blind randomized 12 week placebo controlled trial of Tramadol ER in osteoarthritis of the knee" (dated Oct. 12, 2009).
Declaration of Dr. Okponanabrofa Eradiri of Biovail Corporation in

(56) References Cited

OTHER PUBLICATIONS support of Posters presented at the AAPS Annual Meeting between Oct. 26 and 30, 2003, entitled "Steady State Dose Proportionality of a Novel Formulation of Tramadol HCl Extended Release Tablets" and "The Pharmacokinetics of Novel Once Daily Tramadol Hydrochloride Extended Release Tablets in Healthy Subjects" (dated Oct. 12, 2009).

Office Action in Ex Parte Reexamination proceeding regarding parent U.S. Patent No. 7,413,749, mailed Jan. 27, 2010.

TITRATION DOSING REGIMEN FOR CONTROLLED RELEASE TRAMADOL

1. CROSS-REFERENCE TO RELATED APPLICATIONS

This application is a divisional application of U.S. application Ser. No. 10/800,254, filed Mar. 10, 2004, now U.S. Pat. No. 7,413,749, which claims the benefit of U.S. Provisional Application No. 60/453,848, filed Mar. 11, 2003, the disclosures of which are incorporated by reference herein in their entireties.

2. FIELD OF THE INVENTION

This invention relates to a titration dosing regimen for the administration of controlled release dosage forms of tramadol to patients. The novel titration dosing regimen reduces the occurrence of adverse effects which often result from beginning administration of a controlled release tramadol dosage at the mean level required for adequate analgesia, and thus, greatly reduces the number of patients that discontinue administration of tramadol due to the adverse effects experienced during the introductory dosage period. Consequently, this titration dosing regimen increases the therapeutic benefit of controlled release tramadol by minimizing adverse effects.

3. BACKGROUND OF THE INVENTION

Tramadol, which has the chemical name (+/−)-trans-2-[(dimethylamino)methyl]-1-(3-methoxyphenyl)cyclohexanol, is a centrally acting synthetic opioid analgesic that is effective for the management of moderate to severe pain. After oral administration, tramadol is rapidly absorbed and metabolized into the pharmacologically active metabolite mono-O-desmethyltramadol. Conventional release preparations in the form of capsules, drops and suppositories containing tramadol have been commercially available for many years for use in the treatment of moderate to severe pain.

The prior art addresses the titration dosage regimen for immediate release tramadol. For example, U.S. Pat. No. 6,339,105 discloses a dosage regimen for immediate release tramadol including about 25 mg on days 1 to 3; 50 mg on days 4 to 6; 75 mg on days 7 to 9; 100 mg on days 10 to 12; 150 mg on days 13 to 15 and 200 mg on days 16 to 28. Also disclosed therein is a dosage regimen for immediate release tramadol including 25 mg q.d. on days 1 to 3; 25 mg b.i.d. on days 4-6, 25 mg t.i.d. on days 7 to 9; 25 mg q.i.d. on days 10 to 12; and 50 mg t.i.d. on days 13 to 28. The dosing of a controlled release form is not addressed in U.S. Pat. No. 6,339,105.

Controlled release tramadol is known to elicit adverse effects, including nausea, vomiting, sleepiness, dizziness, itchiness, sedation, dry mouth, sweating and constipation.

Thus, a need exists for the development of an advantageous dosing regimen for a controlled release dosage form of tramadol. More specifically, there exists a need for a dosage regimen for a controlled release tramadol which significantly reduces the occurrence of and concomitant severity of adverse tramadol elicited side effects, and thus, reduces potential discontinuation by patients due to these effects and increases the number of patients who may successfully be treated.

4. DEFINITIONS

The term "controlled release" is defined for purposes of the present invention as the release of the drug (i.e., tramadol) in vitro over a period of time about 12 hours or more, more preferably for periods of about 24 hours or longer. The term "controlled release" is deemed to encompass the term "prolonged release" as that term is used by the Committee on Proprietary Medicinal Products ("CPMP").

Unless specified to the contrary, any reference to any pharmaceutical compound, such as tramadol, throughout this disclosure includes not only that pharmaceutical compound, i.e., the so-called free form of that compound, but also pharmaceutically acceptable derivatives, pharmaceutically acceptable salts of that compound, base forms of that compound, optical isomers of that compound, stereoisomers of that compound, and mixtures of any of the foregoing.

The phrase "pharmaceutically acceptable salt," as used herein, is a salt formed from an acid and the basic group of an active agent or an adverse agent. Generally, examples of such salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate, glubionate and pamoate (i.e., 1,1'-methylene-bis-(2-hydroxy-3-naphthoate)) salts. The term "pharmaceutically acceptable salt" also refers to a salt prepared from an active agent or an adverse agent having an acidic functional group, such as a carboxylic acid or sulfonic acid functional group, and a pharmaceutically acceptable inorganic or organic base. Generally, examples of such bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N,-dimethyl-N-(2-hydroxyethyl)amine, or tri-(2-hydroxyethyl)amine; N-methyl-D-glucamine; and amino acids such as arginine, lysine, and the like.

The term "base form" as used herein, e.g., for tramadol, refers to a salt prepared from tramadol having an acidic functional group, such as a carboxylic acid or sulfonic acid functional group, and a pharmaceutically acceptable inorganic or organic base. Suitable bases include, but are not limited to, hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl, N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N,-dimethyl-N-(2-hydroxyethyl)amine, or tri-(2-hydroxyethyl)amine; N-methyl-D-glucamine; and amino acids such as arginine, lysine, and the like.

The term "tramadol-like side effects" is defined for purposes of the present invention as including, but not limited to, nausea, vomiting, sleepiness, dizziness, itchiness, dry mouth, and constipation.

The term "distractor side effects" is defined for purposes of the present invention as including, but not limited to, toothache, cough, abdominal pain, joint pain, blurry vision, fever, and dyspepsia.

The term "statistically significant" is defined for purposes of the present invention as P<0.04999, where P values are derived from pair-wise comparisons of treatment groups versus placebo from the analysis of variance using Fischer's LSD.

The term "THCR" is defined for purposes of the present invention as tramadol hydrochloride controlled release oral dosage form.

The term "substantially," as used herein, when modifying an adjective or adjective phrase immediately succeeding it, should be understood to mean that adjective or adjective phrase applies to at least about a 95% level, preferably to at least about a 98% level, more preferably to at least a 99% level, for example to at least about a 99.9% level, with respect to the noun or pronoun that the adjective or adjective phrase modifies.

The term "curing" is defined for purposes of the present invention as the heat treatment of the dosage form (or intermediate product) for purposes of obtaining a stabilized final oral pharmaceutical controlled release dosage form. When the formulations of the invention incorporate a polymer as part or all of the hydrophobic retarding agent, it will be appreciated by those skilled in the art that a heat treatment causes a curing effect and that the polymer possibly cross-links with itself into a more stable state. When the formulations of the invention do not incorporate a polymer but rather include a hydrophobic material such as, e.g., hydrogenated vegetable oil or stearyl alcohol, one skilled in the art will appreciate that the heat treatment is more akin to an annealing of the formulation rather than a curing of the polymer. However, for purposes of the present invention, the use of the term "curing" is deemed to encompass both curing and/or annealing.

The terms "stable dissolution profile" and "curing endpoint" are defined for purposes of the present invention as meaning that the cured solid dosage form (e.g., tablet) reproducibly provides a release of the active agent (e.g., tramadol) when placed in an environment of use which is unchanged, even after exposing the cured formulation to accelerated storage conditions. Those skilled in the art will recognize that by "unchanged" it is meant that any change in the release of the active agent from the cured formulation would be deemed insignificant in terms of the desired effect. For pharmaceutical formulations, stability is determined by, e.g., a regulatory agency such as the Food & Drug Administration ("FDA") in the U.S., or the CPMP in Europe, for the purpose of according an expiration date for the formulation.

By the phrase "accelerated storage conditions" it is meant, e.g., storage conditions of elevated temperature and/or elevated relative humidity. Preferably, the phrase "accelerated storage conditions" refers to storage conditions to which the final drug formulation is subjected for the purpose of obtaining regulatory approval (e.g., FDA approval in the U.S.) and an expiration date.

The term "expiration date" is defined for purposes of the present invention as the date designating the time during which a batch of the product (e.g., the cured, coated substrate) is expected to remain within specification if stored under defined conditions, and after which it should not be used.

The term "band range" for purposes of the present invention is defined as the difference in in vitro dissolution measurements of the controlled release formulations when comparing the dissolution profile (curve) obtained by the formulation upon completion of the manufacturing of the coated product (prior to storage) and the dissolution profile obtained after the coated product is exposed to accelerated storage conditions, expressed as the change in percent of the active agent released from the coated product at any dissolution time point along the dissolution curves.

The term "W 50" is defined as the width of the curve of the graphical representation of the in vivo blood plasma concentration of tramadol in ng/ml versus the time elapsed after administration in hours.

5. SUMMARY OF THE INVENTION

In one embodiment, the present invention includes a dosage regimen for administering tramadol to a patient comprising administering: about 75 mg to about 125 mg of tramadol in a controlled release dosage form once-a-day, or q.d., for about 4 to about 10 days; then about 175 mg to about 225 mg of tramadol in a controlled release dosage form once-a-day for about 4 to about 10 days; then about 275 mg to about 325 mg of tramadol in a controlled release dosage form once-a-day for at least 1 day and optionally thereafter.

In another embodiment, the present invention includes a titration dosage regimen comprising administering to one in need thereof 100 mg q.d., or once-a-day, of controlled release tramadol for about seven consecutive days (days 1-7), followed by 200 mg q.d. of controlled released tramadol administered for about the next seven consecutive days (days 8-14), and then 300 mg q.d. of controlled released tramadol administered on about day 15 and optionally thereafter.

The present invention includes titration dosing regimen which either continue to administer controlled release tramadol at a dosage of 300 mg q.d. on days 16 and for a period thereafter, or which increase, decrease or cease the administration of controlled release tramadol to the patient after day 15. For example, the invention includes administering 300 mg q.d. of controlled release tramadol on days 16 through 21.

One embodiment of the invention includes a kit for the administration of a dosage regimen of tramadol comprising:
  instructions to administer the following amounts of tramadol in controlled release oral dosage forms according to the following dosage regimen:
    100 mg of tramadol once-a-day on days 1 through 7;
    200 mg of tramadol once-a-day on days 8 through 14; and
    300 mg of tramadol once-a-day on days 15 through 21, and optionally thereafter; and
  a sufficient quantity of controlled release oral dosage forms of tramadol to administer tramadol according to the dosage regimen.

Additional embodiments include a dosage regimen for administering tramadol to a patient comprising administering: about 175 mg to about 225 mg of tramadol in a controlled release dosage form once-a-day for about 4 to about 10 days; then about 275 mg to about 325 mg of tramadol in a controlled release dosage form once-a-day for at least 1 day and optionally thereafter. For example, the invention includes further administering about 275 mg to about 325 mg for about 6 days to about 14 days, and optionally thereafter.

In another embodiment, the controlled release tramadol titration dosing regimen of the present invention comprises administering 200 mg q.d. controlled release tramadol on days 1 to 7; and 300 mg q.d. on day 8 and optionally for a time thereafter. For example, the present invention includes a titration dosing regimen which further comprises administering controlled release tramadol at a dosage of 300 mg q.d. on days 8 through 21. The present invention also includes administering 300 mg q.d. of controlled release tramadol for a longer or shorter period of time after day 8, as well as either increasing, decreasing and/or ceasing the dosage of controlled release tramadol after day 8.

Another embodiment of the invention includes a kit for the administration of a dosage regimen of tramadol comprising:
   instructions to administer the following amounts of tramadol in controlled release oral dosage forms according to the following dosage regimen:
      200 mg of tramadol once-a-day on days 1 through 7; and
      300 mg of tramadol once-a-day on days 8 through 15, and optionally thereafter; and
   a sufficient quantity of controlled release oral dosage forms of tramadol to administer tramadol according to the dosage regimen.

It has been discovered that, while reaching the most commonly prescribed dose of 300 mg of tramadol, the titration dosage regimen of controlled release tramadol according to the present invention often results in a significant reduction of adverse side effects and significantly better tolerance than starting doses of 300 mg q.d. on day 1.

6. DETAILED DESCRIPTION OF THE INVENTION

In certain embodiments, the present invention includes a dosage regimen for administering tramadol to a patient comprising administering about 75 mg to about 125 mg of tramadol in a controlled release dosage form once-a-day for about 4 to about 10 days; then about 175 mg to about 225 mg of tramadol in a controlled release dosage form once-a-day for about 4 to about 10 days; then about 275 mg to about 325 mg of tramadol in a controlled release dosage form once-a-day for at least 1 day and optionally thereafter.

In one embodiment, the regimen of the present invention is a 21 day titration, whereby 100 mg q.d. controlled release tramadol is administered on days 1 to 7. The dosage of controlled release tramadol is increased to 200 mg q.d. for days 8-14, and then increased again to 300 mg q.d. controlled release tramadol during days 15-21.

An alternative embodiment of the present invention comprises a titration dosing regimen for controlled release tramadol comprising administering to a patient in need thereof 100 mg q.d. controlled release tramadol on days 1 through 7; 200 mg q.d. controlled release tramadol on days 8 through 14; and 300 mg q.d. controlled release tramadol on day 15. Thereafter, the administration of tramadol to the patient may be either continued at the 300 mg dosage level, increased, decreased or terminated in accordance with the patient's needs.

In another embodiment, the present invention includes a kit for the administration of a dosage regimen of tramadol comprising:
   instructions to administer the following amounts of tramadol in controlled release oral dosage forms according to the following dosage regimen:
      100 mg of tramadol once-a-day on days 1 through 7;
      200 mg of tramadol once-a-day on days 8 through 14; and
      300 mg of tramadol once-a-day on days 15 through 21, and optionally thereafter; and
   a sufficient quantity of controlled release oral dosage forms of tramadol to administer tramadol according to the dosage regimen.

The kit may preferably consist of a plurality of oral dosage forms containing amounts of tramadol selected from the group consisting of 100 mg, 200 mg and 300 mg.

In other embodiments, the present invention includes a dosage regimen for administering tramadol to a patient comprising administering about 175 mg to about 225 mg of tramadol in a controlled release dosage form once-a-day for about 4 to about 10 days; then about 275 mg to about 325 mg of tramadol in a controlled release dosage form once-a-day for at least 1 day and optionally thereafter.

In another embodiment, the present invention includes an initial titration dosage regimen for controlled release tramadol comprising administering to a patient in need thereof 200 mg q.d. of controlled release tramadol on days 1 through 7 and 300 mg q.d. of controlled release tramadol on day 8. Thereafter, the dosage level may either remain at 300 mg q.d. of controlled release tramadol or may be either increased, decreased or ceased depending upon the needs of the patient.

In another embodiment, the present invention includes a kit for the administration of a dosage regimen of tramadol comprising:
   instructions to administer the following amounts of tramadol in controlled release oral dosage forms according to the following dosage regimen:
      200 mg of tramadol once-a-day on days 1 through 7; and
      300 mg of tramadol once-a-day on days 8 through 15, and optionally thereafter; and
   a sufficient quantity of controlled release oral dosage forms of tramadol to administer tramadol according to the dosage regimen.

The kit may preferably consist of a plurality of oral dosage forms containing amounts of tramadol selected from the group consisting of 100 mg, 200 mg and 300 mg.

The dosage regimen of the present invention may be practiced by administering any controlled release dosage form containing tramadol. However, in certain embodiments, the controlled release dosage form is an oral dosage form such as, for example, a tablet or capsule.

The tramadol may be present in the controlled release dosage form in any pharmaceutically acceptable form. The controlled release dosage form provides an in vitro release of tramadol for at least about 12 hours or more. In certain embodiments, the controlled release dosage form provides an in vitro release of tramadol for about 24 hours or longer.

6.1 Controlled Release Tramadol Dosage Forms

The present invention encompasses titration dosage regimen for administering any controlled release dosage form of tramadol. Examples of suitable controlled release tramadol oral dosage forms may be found in U.S. Pat. Nos. 6,326,027 and 6,306,438, the disclosures of which are expressly incorporated herein in their entirety. The following detailed description sets forth exemplary formulations and methods of manufacture for oral THCR which may be administered in accordance with the present invention.

For example, in order to obtain a controlled release tramadol oral dosage form, the tramadol may be homogeneously combined with a sufficient amount of one or more hydrophobic (release-retardant) material(s), such as a wax or a wax-like material ("wax-like substance").

The hydrophobic material(s) used in such controlled release tramadol formulations may include, for example, material(s) such as, acrylic or methacrylic polymers or copolymers, alkylcelluloses, zein, shellac, a natural or synthetic wax or oil, including but not limited to, hydrogenated fats such as hydrogenated vegetable oil, hydrogenated castor oil, microcrystalline wax, normal waxes, beeswax, carnauba wax, paraffin, or glyceryl monostearate, and may have a melting point of from 45 to 140° C., preferably 50 to 110° C. Ammonio methacrylate copolymers are suitable, for example.

The hydrophobic material(s) may be any pharmaceutically acceptable acrylic polymer, including but not limited to, any of acrylic acid and methacrylic acid copolymers, methyl methacrylate copolymers, ethoxyethyl methacrylates, cynaoethyl methacrylate, aminoalkyl methacrylate copolymer, poly(acrylic acid), poly(methacrylic acid), methacrylic acid alkylamide copolymer, poly(methyl methacrylate), poly(methacrylic acid) (anhydride), methyl methacrylate, polymethacrylate, poly(methyl methacrylate), poly(methyl methacrylate) copolymer, polyacrylamide, aminoalkyl methacrylate copolymer, poly(methacrylic acid anhydride), and glycidyl methacrylate copolymers.

The acrylic polymer may also be comprised of one or more ammonio methacrylate copolymers. Ammonio methacrylate copolymers are well known in the art, and are fully polymerized copolymers of acrylic and methacrylic acid esters with a low content of quaternary ammonium groups. Examples of such acrylic polymers are acrylic resin lacquers commercially available from Rohm Pharma under the Tradename Eudragit™.

Alternatively or in addition to the above materials, the wax or wax-like substance(s) used in the formulations of the present invention may include fatty alcohols, fatty acid esters, fatty acid glycerides (mono-, di-, and tri-glycerides), higher aliphatic (e.g., $C_{10}$-$C_{20}$) acids, higher aliphatic (e.g., $C_{12}$-$C_{36}$) alcohols, long chain fatty acids, and mixtures thereof. In certain embodiments, useful water-insoluble wax-like substances may be those with a water-solubility that is lower than about 1:5,000 (w/w). The higher aliphatic alcohol may be, for example, lauryl alcohol, myristyl alcohol or stearyl alcohol.

One particularly suitable controlled release matrix includes one or more alkylcelluloses and one or more $C_{12}$-$C_{36}$ aliphatic alcohols. The alkylcellulose is preferably $C_1$-$C_6$ alkyl cellulose, particularly ethylcellulose, and the higher aliphatic alcohol is preferably stearyl alcohol.

The release of the active agent from the controlled release formulation can be further influenced, i.e., adjusted to a desired rate, by the addition of one or more release-modifying agents into the matrix. The release-modifying agents may comprise one or more water-soluble hydrophilic polymers in order to modify the release characteristics of the formulation. Examples of suitable hydrophilic polymers include cellulose ethers, such as hydroxyalkylcelluloses (e.g., hydroxypropylmethylcellulose), and carboxyalkylcelluloses, acrylic resins and protein-derived materials. Also, synthetic water-soluble polymers may be used, such as polyvinylpyrrolidone, cross-linked polyvinylpyrrolidone, polyethylene oxide, etc., and polysaccharides, e.g., pullulan, dextran, sucrose, glucose, fructose, mannitol, lactose, mannose, galactose, sorbitol and mixtures thereof.

Semipermeable polymers may also be incorporated in the matrix to change the release characteristics of the formulation. Such semipermeable polymers include, for example, cellulose acylates, acetates, and other semipermeable polymers such as those described in U.S. Pat. No. 4,285,987, as well as the selectively permeable polymers formed by the coprecipitation of a polycation and a polyanion as disclosed in U.S. Pat. Nos. 3,173,876; 3,276,586; 3,541,005; 3,541,006 and 3,546,142.

It may be desirable to also add a plasticizer when using certain hydrophobic polymers. Examples of suitable plasticizers for ethylcellulose include water insoluble plasticizers such as dibutyl citrate, dibutyl sebacate, diethyl phthalate, triethyl citrate, tributyl citrate, and triacetin, although it is possible that other water-insoluble plasticizers (such as acetylated monoglycerides, phthalate esters, castor oil, etc.) may be used. Examples of suitable plasticizers for acrylic polymers include citric acid esters such as triethyl citrate, tributyl citrate, dibutyl phthalate, and possibly 1,2-propylene glycol, polyethylene glycols, propylene glycol, diethyl phthalate, castor oil, and triacetin, although it is possible that other water-insoluble plasticizers (such as acetylated monoglycerides, phthalate esters, castor oil, etc.) may be used. However, controlled release tramadol dosage forms can be prepared without the presence of a plasticizer.

In addition to the foregoing, the controlled release tramadol formulations may include pharmaceutically acceptable carriers and excipients. Specific examples of pharmaceutically acceptable carriers and excipients that may be used to formulate oral dosage forms are described in the Handbook of Pharmaceutical Excipients, American Pharmaceutical Association (1986), incorporated by reference herein. Techniques and compositions for making solid oral dosage forms are described in Pharmaceutical Dosage Forms: Tablets (Lieberman, Lachman and Schwartz, editors) Second Edition, published by Marcel Dekker, Inc., incorporated by reference herein. Techniques and compositions for making tablets (compressed and molded), capsules (hard and soft gelatin) and pills are also described in Remington's Pharmaceutical Sciences, (Arthur Osol, editor), 1553-1593 (1980), incorporated by reference herein. Pharmaceutically acceptable ingredients which are conventional in the pharmaceutical art include diluents, lubricants, binders, granulating aids, colorants, flavorants, surfactants, pH adjusters, anti-adherents and glidants, e.g., dibutyl sebacate, ammonium hydroxide, oleic acid and colloidal silica.

The total amount of tramadol in the controlled release dosage form may vary within wide limits, including, but not limited to from about 20 to about 80%, preferably from about 40 to about 60%, and most preferably from about 45 to about 55%, by weight. The total amount of hydrophobic material in the controlled release dosage form may also vary widely, including but not limited to, from about 80 to about 20%, by weight.

In one embodiment, the controlled release tramadol dosage form suited for once-a-day dosing may have an in vitro release rate corresponding to the following % rate of tramadol released: from about 0 to about 50% tramadol released after about 1 hour; from about 0 to about 75% tramadol released after about 2 hours; from about 10 to about 95% tramadol released after about 4 hours; from about 35 to about 100% tramadol released after about 8 hours; from about 55 to about 100% tramadol released after about 12 hours; from about 70 to about 100% tramadol released after about 16 hours; and more than about 90% tramadol released after about 24 hours.

In another embodiment, the controlled release tramadol dosage form suited for once-a-day dosing may have an in vitro release rate corresponding to the following % rate of tramadol released: from about 0 to about 30% tramadol released after about 1 hour; from about 0 to about 40% tramadol released after 2 hours; from about 3 to about 55% tramadol released after about 4 hours; from about 10 to about 65% tramadol released after about 8 hours; from about 20 to about 75% tramadol released after about 12 hours; from about 30 to about 88% tramadol released after about 16 hours; from about 50 to about 100% tramadol released after about 24 hours; and more than about 80% tramadol released after about 36 hours.

More preferably, a controlled release tramadol dosage form particularly suited for once-a-day dosing has an in vitro release rate as follows: from about 15 to about 25% tramadol released after about 1 hour; from about 25 to about 35% tramadol released after about 2 hours; from about 30 to about 45% tramadol released after about 4 hours; from about 40 to about 60% tramadol released after about 8 hours; from about 55 to about 70% tramadol released after about 12 hours; and from about 60 to about 75% tramadol released after about 16 hours.

In certain embodiments, the controlled release tramadol dosage form suitable for once-a-day dosing may have a $T_{max}$ in the range of about 3 to about 8 hours, preferably about 4 to about 5 hours and a $W_{50}$ value in the range about 10 to about 33 hours.

The in vitro release rates mentioned herein are, except where otherwise specified, those obtained by measurement using the USP Apparatus 2 (Paddle Method) at 100 rpm in pH 6.5 phosphate buffer at 37° C.

The controlled release formulation preferably contains an analgesically effective amount of tramadol, which may conveniently be in the range of from about 50 to about 300 mg, especially 100, 200 or 300 mg (calculated as tramadol hydrochloride) per dosage unit.

The controlled release formulations slowly release the tramadol, e.g., when ingested and exposed to gastric fluids, and then to intestinal fluids. The controlled release profile of the formulations can be altered, for example, by varying the amount of hydrophobic polymer, by varying the amount of plasticizer relative to hydrophobic polymer, by the inclusion of additional ingredients or excipients, by altering the method of manufacture, etc.

6.2 Manufacture of Controlled Release Tramadol Dosage Form

The present invention includes the dosing of controlled release tramadol, regardless of the particular formulation or method of manufacture of the dosage form. The following exemplary methods of manufacturing the controlled release tramadol dosage form are suitable. Additionally, suitable methods of manufacturing the controlled release tramadol dosage form include those set forth in U.S. Pat. Nos. 6,306,438 and 6,326,027, the disclosures of each are expressly incorporated herein by reference.

One acceptable process for preparing a controlled release preparation for use in the present invention comprises incorporating tramadol in a controlled release matrix, for example by (a) granulating a mixture comprising tramadol or a pharmaceutically acceptable salt thereof and one or more alkylcelluloses, (b) mixing the alkylcellulose containing granules with one or more $C_{12-36}$ aliphatic alcohols; and optionally (c) shaping and compressing the granules, and film coating, if desired.

Another suitable method for manufacturing the controlled release dosage form is as follows:

(a) granulating a mixture comprising tramadol or a pharmaceutically acceptable salt thereof, lactose and one or more alkylcelluloses with one or more $C_{12-36}$ aliphatic alcohol; and, optionally, (b) shaping and compressing the granules, and film coating, if desired.

The controlled release dosage form may also be prepared in the form of film coated spheroids by (a) granulating the mixture comprising tramadol or a pharmaceutically acceptable salt thereof and a spheronizing agent;

(b) extruding the granulated mixture to give an extrudate;

(c) spheronizing the extrudate until spheroids are formed; and (d) coating the spheroids with a film coat.

The controlled release dosage form may also be prepared by a process which comprises forming a mixture of dry active ingredient and fusible release control materials followed by mechanically working the mixture in a high speed mixer with an energy input sufficient to melt or soften the fusible material whereby it forms particles with the active ingredient. The resultant particles, after cooling, are suitably sieved to give particles having a size range from about 0.1 to about 3.0 mm in any dimension.

The sustained release dosage form may comprise a capsule filled with controlled release particles comprising the active ingredient, a hydrophobic material or diluent and optionally a hydrophillic release modifier.

The hydrophilic release modifier may be a water soluble fusible material, such as a polyethylene glycol, and may be a particulate material, such as dicalcium phosphate or lactose.

Another acceptable process for the manufacture of a controlled release tramadol dosage form comprises (a) mechanically working in a high-speed mixer, a mixture of tramadol in particulate form and a particulate, hydrophobic material or diluent having a melting point from about 35 to about 140° C. and optionally a release control component comprising a water soluble fusible material, or a particulate soluble or insoluble organic or inorganic material, at a speed and energy input which allows the carrier or diluent to melt or soften, whereby it forms agglomerates;

(b) breaking down the larger agglomerates to give controlled release seeds; and (c) continuing mechanically working, with optionally a further addition of low percentage of the carrier or diluent; and.

(d) optionally repeating steps (c) and possibly (b) one or more times.

The resulting particles may be sieved to eliminate any over-or undersized material then formed into the desired dosage units by, for example, encapsulation into hard gelatin capsules containing the required dose of the active substance or by compressing into tablets.

In this method, all the tramadol may be added in step (a) together with a major portion of the hydrophobic material used.

Stage (a) of the process may be carried out in conventional high speed mixers with a standard stainless steel interior, e.g., a Collette Vactron 75 or equivalent mixer. The mixture may be processed until a bed temperature about 40° C. or above is achieved and the resulting mixture acquires a cohesive granular texture, with particle sizes ranging from about 1-3 mm to fine powder in the case of non-aggregated original material. Such material may generally have the appearance of agglomerates which upon cooling below 40° C. have structural integrity and resistance to crushing between the fingers. At this stage the agglomerates may be of an irregular size, shape and appearance.

The agglomerates are preferably allowed to cool. The temperature to which it cools is not critical and a temperature in the range room temperature to 37° C. may be conveniently used.

The agglomerates are broken down by any suitable means, which will comminute oversize agglomerates and produce a mixture of powder and small particles preferably with a diameter under 2 mm. The particles may be classified by size by using a Jackson Crockatt granulator with a suitable sized mesh, or a Comil with an appropriate sized screen. A mesh size of 12 has been found adequate.

The classified material is returned to the high speed mixer, and processing is continued. It is believed that this leads to agglomeration of the finer particles into particles of uniform size range.

Processing of the classified materials may be continued until the hydrophobic material used begins to soften or melt and optionally additional hydrophobic material may then be added. Mixing is continued until the mixture has been transformed into particles of the desired predetermined size range.

In order to obtain uniform energy input into the ingredients in the high speed mixer at least part of the energy may be supplied by means of microwave energy. Energy may also be delivered through other means such as by a heating jacket or via the mixer impeller and chopper blades.

After the particles have been formed they are cooled or allowed to cool, and may then be sieved to remove any cover or undersized material.

The resulting particles may be used to prepare dosage units in the form of e.g. tablets, capsules, multiparticulates or granules in manners known per se. The controlled release formulations according to the invention may conveniently be film coated using any film coating material conventional in the pharmaceutical art. Preferably an aqueous film coating is used.

The granules or tablets may be film-coated according to well known methods. For example, the granules may be film-coated and then either divided into unit doses of tramadol (e.g., and placed in a gelatin capsule), or compressed into a tablet. The film coating may be accomplished prior to or after a curing step.

In other embodiments, the film-coating substantially comprises a hydrophilic polymer and does not affect the rate of release of the drug from the formulation. The film-coatings which may be used preferably are capable of producing a strong, continuous film that is smooth and elegant, capable of supporting pigments and other coating additives, non-toxic, inert, and tack-free.

In certain embodiments, the film-coating may contribute to the release properties of the dosage form. In such cases, the dosage form, e.g., granules or tablets, may be coated with a sufficient amount of hydrophobic material to obtain a weight gain level from about 1 to about 30 percent. The solvent which is used for the hydrophobic material may be any pharmaceutically acceptable solvent, including water, methanol, ethanol, methylene chloride and mixtures thereof. It is preferable however, that the coatings be based upon aqueous dispersions of the hydrophobic material. The hydrophobic polymer used in such film-coatings may comprise, for example, a pharmaceutically acceptable acrylic polymer, including but not limited to acrylic acid and methacrylic acid copolymers, or an alkylcellulose such as ethylcellulose, such as a commercially-available aqueous dispersion of ethylcellulose known as Aquacoat™ (FMC Corp., Philadelphia, Pa., U.S.A.). The acrylic polymer in certain instances may be one or more ammonio methacrylate copolymers commercially available from Rohm Pharma under the Tradename Eudragit™.

To form a controlled release tablet dosage form, particles prepared as described above will be admixed or blended with the desired excipient(s), e.g., one or more of the standard excipients such as diluents, lubricants, binding agents, flow aids, disintegrating agents, surface active agents or water soluble polymeric materials, if any, using conventional procedures, e.g., using a Y-cone or bin-blender. The resulting mixture may then be compressed according to conventional tableting procedure using a suitable size tableting mold. Tablets can be produced using conventional tableting machines, such as a standard single punch F3 Manesty machine or Kilian RLE15 rotary tablet machine. The tablets may be any suitable shape, such as round, oval, biconcave, hemispherical, etc.

Suitable diluents include microcrystalline cellulose, lactose and dicalcium phosphate. Suitable lubricants are e.g. magnesium stearate and sodium stearyl fumarate. Suitable binding agents are, e.g., hydroxypropyl methyl cellulose, polyvidone and methyl cellulose.

Suitable disintegrating agents include starch, sodium starch glycolate, crospovidone and croscarmalose sodium. Suitable surface active agents include Poloxamer 188R, Polysorbate 80 and sodium lauryl sulfate. Suitable flow aids include talc colloidal anhydrous silica. Suitable water soluble polymers include polyethylene glycol ("PEG") with molecular weights in the range 1000 to 6000.

Generally, even with a highly water soluble active agent as tramadol, tablets formed by compression according to standard methods give very low in vitro release rates of the active ingredient e.g. corresponding to release over a period of greater than 24 hours and, in certain embodiments, more than 36 hours. However, suitable selection of the materials used in forming the particles and in the tableting and the proportions in which they are used enables a significant degree of control in the ultimate dissolution and release rates of the tramadol or salt thereof from the compressed tablets. For instance a higher loading of the drug will typically be associated with increased release rates; the use of larger proportions of water soluble fusible materials in the particles or surface active agent in the tableting formulation will also be associated with a higher release rate of the active ingredient. By controlling the relative amounts of these ingredients it is possible to adjust the release profile of the tramadol.

In certain embodiments, the controlled release tramadol dosage forms used in the present invention may be prepared in a manner that provides stability. The dosage form may be cured to an endpoint at which the dosage form provides a reproducible stable dissolution profile, even after exposure to accelerated storage conditions or after prolonged storage at room temperature. The dosage form may be cured by exposure to prolonged elevated temperatures in order to achieve stability. In situations where the hydrophobic material includes only a wax-like substance, the curing may be accomplished at a temperature from about 35° C. to about 65° C., for a sufficient time period until stability is achieved, such as for a time period from about 4 to about 72 hours. In other embodiments, the curing is conducted at a temperature from about 40° C. to about 60° C., for a time period from about 5 to about 48 hours, preferably at least about 24 hours. Suitable curing times which achieve the intended result of a stabilized dosage form are known to those of skill in the art.

The curing endpoint may be determined by comparing the dissolution profile of the cured dosage form immediately after curing (hereinafter referred to as "the initial dissolution profile") to the dissolution profile of the dosage form after exposure to accelerated storage conditions or prolonged storage at room temperature. Generally, the curing endpoint may be determined by comparing the dissolution profile of the formulation after exposure to accelerated storage conditions of, e.g., 37° C./80% RH or 40° C./75% RH for a time period of one month to the initial dissolution profile. However, the curing endpoint may be further confirmed by continuing to expose the cured, coated formulation to accelerated storage conditions for a further period of time and comparing the dissolution profile of the formulation after further exposure of, e.g., two months and/or three months, to the initial dissolution profile obtained.

In certain embodiments, the curing endpoint is attained when the data points plotted along a graph of the dissolution curve obtained after, e.g., exposure to accelerated conditions of 1-3 months, show a release of the active agent (tramadol) which does not vary at any given time point by more than about 20% of the total amount of active agent released when compared to in vitro dissolution conducted prior to storage.

Such a difference in the in vitro dissolution curves is referred to in the art as a "band range" or a "band width". In certain embodiments, the band range may be less than 10% to 15% of the total amount of active agent released.

A generally accepted accelerated test employed according to FDA guidelines relates to the storage of a drug product (e.g., in its container and package) at 80% Relative Humidity (RH) and 37° C. (1985 FDA guidelines). If the product holds up for, e.g., three months under these conditions (chemical stability, dissolution, and physical characteristics), then the drug product will be accorded, e.g., a two year expiration date. This accelerated test may also be conducted at 75% RH and 40° C. It has been proposed that long-term storage testing be conducted for pharmaceutical formulations at 25° C.+/−2° C. at not less than 60% RH+/−5% for a minimum time period of 12 months. It has been further proposed that accelerated testing be conducted for pharmaceutical formulations at 40° C.+/−2° C. at 75% RH+/−5% for a minimum time period of 6 months. All of the above-mentioned accelerated testing criteria and others are deemed equivalent for purposes of the present invention, with regard to the determination of stability and the determination of the curing endpoint.

7. EXAMPLES

7.1 Example 1

Controlled release tramadol hydrochloride formulations were developed for the relief of mild to moderate pain by administration once a day, to reduce the frequency of dosing. A clinical study, as described below, was conducted using the following products.

I. Controlled Release Tramadol Dosage Forms

A) 200 mg Tramadol HCl-Controlled Release Tablet

| Ingredients | Mg/Tablet |
| --- | --- |
| Tramadol HCl | 200.0 |
| Ethocel Std 7 Premium | 74.0 |
| Stearyl alcohol | 74.0 |
| Talc (lubricant) | 7.4 |
| Magnesium stearate (lubricant) | 3.7 |
| Total | 359.1 |

The tablets are further coated with 4.5% Opadry Beige dispersed in water.

Controlled release tramadol oral tablets were made according to the above formulation utilizing the following process:
1. Blend all ingredients except for lubricants in a V-blender.
2. Place the mixture in a powder feeder connected to a Leistritz ZSE-27 twin screw extruder having multiple heating zones.
3. Set the temperatures of the extruder heating zones 2 through 6 to 70° C., zones 7 and 8 to 75° C., zones 9 and 10 to 85° C., and the die to 100° C.
4. Set the extruder screw rotation speed to 200 rpm.
5. Start the feeder and conveyor.
6. After the excipients are melted and the drug is embedded in the molten mixture, the viscous mass is extruded into multiple strands of about 3 mm in diameter.
7. Allow the extrudate to congeal and harden while being carried away on a conveyor belt.
8. Break the extrudate into rods of about one inch in length using a pelletizer.
9. Mill the extrudate using a Fitzmill.
10. Lubricate the sized extrudate with required amounts of magnesium stearate and talc by blending in a V-blender.
11. Compress the lubricated blend into tablets using a tablet press equipped with suitable tooling. In this example, the THCR dosage form made was a 200 mg tablet having a size of 0.2320"×0.5720" having an indented line bisecting each side.
12. Cure the tablets at 50° C. for 24 hours in a Hotpack oven.
13. Coat the tablets with Opadry dispersed in water using a Compulab Coater equipped with a 48 inch pan.

In vitro measurements of the tramadol HCl controlled release tablets were conducted using the following dissolution method (No. 340-DS1-1AS):
1. Apparatus—USP Type II (Paddle), 100 RPM
2. Medium—900 ml 55 mM potassium phosphate buffer, pH 6.5, (37° C.
3. Sampling time—2, 8, 24 hours
4. Analytical test—High Performance Liquid Chromatography using Waters Symmetry C-18 column and UV detection at 270 nm.

| Dissolution Results for THCR 200 | |
| --- | --- |
| Time (hr) | % Dissolved |
| 2 | 27 |
| 8 | 52 |
| 24 | 82 |

B) 100 mg Tramadol HCl-Controlled Release Dosage

Manufacturing Process
1. Break tramadol 200 mg controlled release tablets, which were made in accordance with above-described formulation and method, into two halves manually at the score.
2. Fill one half tablet into Size 0 gelatin capsules.
3. Back fill the capsule with lactose.

Dissolution Method

The dissolution test method was the same as that described above with respect to the 200 mg tablet.

Dissolution Results

| Dissolution Results for THCR 100 (capsule containing half tablet of THCR 200) | |
| --- | --- |
| Time (hr) | % Dissolved |
| 2 | 39 |
| 8 | 69 |
| 24 | 94 |

C) 300 mg Tramadol Controlled Release Dosage

Dosages of 300 mg tramadol controlled release tablets were provided in the form of one 200 mg tramadol controlled release tablet, as prepared above, and one 100 mg tramadol controlled release dosage, also as prepared above.

II. Clinical Study and Results

The effect of various dose titration schedules of tramadol hydrochloride controlled release tablets was studied in a multiple-dose, randomized, double-blind, parallel group, placebo-controlled, multi-center, outpatient study. A total of two hundred five (205) male subjects enrolled in the study and were randomly assigned into one of four treatment groups. The planned total number of evaluable subjects was 200, with 50 subjects in each treatment group. Treatment groups were titrated over a dosing period lasting 21 days at three different rates to achieve the study target dose of 300 mg/day: the "THCR 100 Group" followed a $100_{Day\ 1\text{-}7}$ to $200_{Day\ 8\text{-}14}$ to $300_{Day\ 15\text{-}21}$ mg q.d. dosing regimen; the "THCR 200 group" followed a $200_{Day\ 1\text{-}7}$ to $300_{Day\ 8\text{-}14}$ to $300_{Day\ 15\text{-}21}$ mg q.d. dosing regimen; and the "THCR 300 group" followed a $300_{Day\ 1\text{-}7}$ to $300_{Day\ 8\text{-}14}$ to $300_{mg\ q.d.\ Day\ 15\text{-}21}$ mg q.d. dosing regimen. The fourth group received placebos during the course of the study. Study medication or placebo was always administered once per day or q.d. One hundred ninety-three (193) subjects completed the study. Observed adverse events were assessed. As used herein, an adverse event or side effect includes any noxious, pathologic, or unintended change in anatomical, physiological, or metabolic functions as indicated by physical signs, symptoms, or laboratory changes occurring in any phase of the clinical study, whether or not considered drug-related.

All study medication was packaged in bottles to be dispensed to the subjects on a weekly basis. All subjects were given two bottles weekly: bottle A, containing THCR 200 mg tablets or matching placebo tablets; and bottle B, containing encapsulated half-tablet (100 mg) THCR 200 mg tablets or matching placebo capsules. Each participant was given detailed instructions on how to take the study medication. Specifically, each participant was directed to take one tablet from bottle A and one capsule from bottle B by mouth at 8:00 am (+/−2 hours). The treatment group which a participant belonged to determined whether the tablets and/or capsules in the participant's bottles contained THCR or placebo.

As shown in Table 1, entitled "Mean Severity of Tramadol-like and Distractor-Elicited Side Effects", the study results showed that the titration dosage regimen of controlled release tramadol in accordance with the instant invention, as seen in the THCR 100 Group ($100_{Day\ 1\text{-}7}$ to $200_{Day\ 8\text{-}14}$ to $300_{Day\ 15\text{-}21}$ mg q.d.) and in the THCR 200 Group ($200_{Day\ 1\text{-}7}$ to $300_{Day\ 8\text{-}14}$ to $300_{Day\ 15\text{-}21}$ each mg q.d.) treatment groups, resulted in statistically significant lower mean severity of adverse tramadol elicited side effects than in the THCR 300 Group ($300_{Day\ 1\text{-}7}$ to $300_{Day\ 8\text{-}14}$ to $300\ Day_{15\text{-}21}$ mg q.d.), particularly for the THCR 100 Group during days 1 to 14 and for the THCR 200 Group for days 1 to 7, when the mean severity of the noted adverse effects did not exceed those of the placebo group in a statistically significant manner.

More specifically, whenever subjects were administered 300 mg q.d. THCR (the THCR 100 Group, for days 15 to 21; the THCR 200 Group, for days 8 to 14 and 15 to 21; and the THCR 300 Group, for all 3 periods), the difference of the mean severity of elicited side effects (particularly with respect to the most common side effect of nausea) was significant compared to the placebo group. Thus, starting with THCR 100 mg q.d. or 200 mg q.d. was similar to placebo and well tolerated. However, starting with THCR 300 mg q.d. was distinct in terms of side effects from the other week 1 doses, and was not as well tolerated. In fact, as shown in Table 2, entitled "Tolerability Over All 21 Days", a higher incidence of nausea, constipation, dizziness and pruritus occurred in the THCR 300 Group compared with the THCR 200 Group and the THCR 100 Group.

TABLE 1

Mean Severity of Tramadol-like and Distractor-Elicited Side Effects

| | | Days 1-7 | Days 8-14 | Days 15-21 | Overall |
|---|---|---|---|---|---|
| Placebo (N = 49) | | | | | |
| Tramadol-like side effects | Mean ± SEM | .17 ± .035 | .13 ± .027 | .11 ± .023 | .138 ± .0218 |
| Distractor side effects | Mean ± SEM | .09 ± .040 | .05 ± .015 | .03 ± .015 | .061 ± .0179 |
| THCR 100 (N = 47) Group (100/200/300) | | | | | |
| Tramadol-like side effects | Mean ± SEM | .28 ± .035 | .22 ± .033 | .29$^a$ ± .040 | .258$^a$ ± .0283 |
| Distractor side effects | Mean ± SEM | .10 ± .021 | .05 ± .013 | .08 ± .017 | .077 ± .0132 |
| THCR 200 (N = 48) Group (200/300/300) | | | | | |
| Tramadol-like side effects | Mean ± SEM | .29 ± .045 | .31$^a$ ± .046 | .25$^a$ ± .039 | .287$^a$ ± .0382 |
| Distractor side effects | Mean ± SEM | .05 ± .014 | .06 ± .019 | .05 ± .017 | .053 ± .0120 |
| THCR 300 (N = 49) Group (300/300/300) | | | | | |
| Tramadol-like side effects | Mean ± SEM | .43$^{a,b,c}$ ± .056 | .30$^a$ ± .036 | .28$^a$ ± .042 | .337$^a$ ± .0367 |
| Distractor side effects | Mean ± SEM | .10 ± .025 | .08 ± .015 | .08 ± .019 | .084 ± .0149 |
| Treatment comparisons * (tramadol-like) | | s | s | s | s |
| Treatment comparisons * (distractor) | | ns | ns | ns | ns |

Severity was assessed on a numerical scale: 0 = none; 1 = mild; 2 = moderate; 3 = severe; 4 = intolerable.

The mean severity of the 7 tramadol-like elicited side effects was pooled. The mean severity of the 7 distractor-elicited side effects was pooled. These were then assessed for the 3 treatment periods and overall 21 days of the study.

Boldface indicates statistical significance.

$^a$= significance compared to placebo;

$^b$= significance compared to THCR 100 mg q.d.;

$^c$= significance compared to THCR 200 mg q.d.

Pair-wise comparisons were derived from Fisher's LSD.

* Overall treatment comparison used ANOVA.

ns = nonsignificance;

s = significance

TABLE 2

| | | Group Mean Scores | | | | Effect Size[a] | | |
|---|---|---|---|---|---|---|---|---|
| | | THCR | THCR | THCR | | | (p Value)[b] | |
| Parameter | Placebo (PBO) | 100 Group (100/200/300) | 200 Group (200/300/300) | 300 Group (300/300/300) | SD | Pooled SD THCR 100 (100/200/300) | THCR 200 (200/300/300) | THCR 300 (300/300/300) |
| DOAR | 0 | 0 | 0 | 0 | 0 | 0 | 0 | 0 |
| Spontaneously reported adverse events | 1.78 | 3.28 | 3.33 | 4.39 | 3.14 | 0.48 (.0202) | 0.50 (.0156) | 0.83 (<.0001) |
| Overall subjective side-effect experience[c] | 0.33 | 0.53 | 0.49 | 0.59 | 0.47 | 0.42 (0.478) | 0.35 (.0935) | 0.55 (.0077) |
| Combined 7 tramadol-like side effects[c] | 0.14 | 0.26 | 0.29 | 0.34 | 0.22 | 0.54 (.0106) | 0.67 (.0013) | 0.90 (<.0001) |
| Combined 7 distractor-elicited side effects[c] | 0.06 | 0.08 | 0.05 | 0.08 | 0.10 | 0.16 (.4442) | −0.08 (.6974) | 0.22 (.2724) |
| Elicited side effect: nausea[c] | 0.07 | 0.15 | 0.21 | 0.28 | 0.34 | 0.23 (.266) | 0.41 (.0496) | 0.62 (.0028) |
| Elicited side effect: vomiting[c] | 0.01 | 0.10 | 0.10 | 0.08 | 0.24 | 0.36 (.086) | 0.36 (.0824) | 0.28 (.1684) |
| Elicited side effect: dizziness[c] | 0.06 | 0.23 | 0.18 | 0.43 | 0.37 | 0.44 (.0347) | 0.33 (.1128) | 0.99 (<.0001) |

[a] = Effect sizes are compared to placebo
[b] = P values are derived from pairwise comparisons of treatment groups vs placebo from the analysis of variance using Fisher's LSD. Differences are statistically significant if P < 0.0499.
[c] = Mean scores are the least squares mean severity on a 0 to 4 scale, where 0 = none, 1 = mild, 2 = moderate, 3 = severe, and 4 = intolerable.
DOAR = dropout due to adverse reaction.

In summary, the titration regimen starting with doses of THCR at 100 mg q.d. or 200 mg q.d., respectively, to reach the most commonly prescribed effective daily dose of 300 mg q.d. leads to significantly better subject tolerability than starting therapy with doses of 300 mg q.d., and, surprisingly, in some cases is as well tolerated as placebo. The use of a titration dosing regimen according to the present invention, as compared to a dosing regimen of 300 mg q.d. controlled release tramadol on day 1 and thereafter, exhibited significant improvements in subject tolerability of controlled release tramadol based on starting dose and titration schedule. For the most common side effects, there was a clear statistically significant titration schedule response, such that the THCR 100 Group ($100_{Day\ 1-7}$ to $200_{Day\ 8-14}$ to $300_{Day\ 15-21}$) dosing regimen was superior to the THCR 200 Group ($200_{Day\ 1-7}$ to $200_{Day\ 8-14}$ to $300_{Day\ 15-21}$) dosing regimen which was superior to the THCR 300 Group ($300_{Day\ 1-7}$ to $300_{Day\ 8-14}$ to $300_{Day\ 15-21}$) dosing regimen, in terms of tolerability.

7.2 Example 2

A more preferable way of formulating 100 mg tramadol HCl controlled release tablets is according to the following formulation:

Formula (100 mg/tablet)

| Ingredients | Mg/Tablet |
|---|---|
| Tramadol HCl | 100.0 |
| Ethocel Std 7 Premium | 41.5 |
| Stearyl alcohol | 41.5 |
| Talc | 3.8 |
| Magnesium stearate | 1.9 |
| Total | 188.7 |

The tablets are further coated with 2.5% Opadry White dispersed in water.

The manufacturing process is the same as that described above in Example 1, with respect to THCR 200 mg tablets.

The following table sets forth dissolution data for such THCR 100 mg tablets. The dissolution method is the same as that described above in Example 1 with respect to THCR 200 mg tablets.

Dissolution Results for 100 mg tablet

| Time (hr) | % Dissolved |
|---|---|
| 2 | 27 |
| 8 | 52 |
| 24 | 82 |

7.3 Example 3

A more preferable way of formulating 300 mg tramadol HCl controlled release tablets is to make a single 300 mg tablet as follows:

Formula (300 mg/tablet)

| Ingredients | Mg/Tablet |
|---|---|
| Tramadol HCl | 300.0 |
| Ethocel Std 7 Premium | 100.0 |
| Stearyl alcohol | 100.0 |
| Talc | 10.0 |
| Magnesium stearate | 5.0 |
| Total | 515.0 |

The tablets are further coated with 4.5% Opadry Beige dispersed in water.

The manufacturing process is the same as that described above in Example 1 with respect to THCR 200 mg tablets.

The following table sets forth dissolution data for such THCR 300 mg tablets. The dissolution method is the same as that described above in Example 1 with respect to THCR 200 mg tablets.

Dissolution Results for THCR 300

| Time (hr) | % Dissolved |
|---|---|
| 2 | 33 |
| 8 | 60 |
| 24 | 89 |

All patents, applications, publications, test methods, literature and other material cited above are hereby incorporated by reference.

We claim:

1. A dosage regimen for administering tramadol to a patient for the treatment of pain comprising administering: about 100 mg of tramadol in a controlled release dosage form once-a-day on days 1 through 7; then about 200 mg of tramadol in a controlled release dosage form once-a-day on days 8 through 14; then about 300 mg of tramadol in a controlled release dosage form once-a-day on day 15 and optionally thereafter.

2. The dosage regimen of claim 1 wherein the controlled release dosage forms are each oral dosage forms.

3. The dosage regimen of claim 2 wherein the tramadol is present in each oral dosage form in the form of tramadol hydrochloride.

4. The dosage regimen of claim 3 each oral dosage form provides in vitro release of tramadol hydrochloride for about 24 hours or longer.

5. The dosage regimen of claim 1 further comprising administering about 300 mg of tramadol in a controlled release dosage form once-a-day on days 15 through 21 and optionally thereafter.

6. The dosage regimen of claim 5 wherein 100 mg of tramadol is administered in a controlled release dosage form on days 1 through 7; 200 mg of tramadol is administered in a controlled release dosage form on days 8 through 14; and 300 mg of tramadol is administered in a controlled release dosage form on days 15 through 21 and optionally thereafter.

7. The dosage regimen method of claim 6 wherein the tramadol is present in each oral dosage form in the form of tramadol hydrochloride.

8. The dosage regimen method of claim 7 wherein each oral dosage form provides an in vitro release of tramadol hydrochloride of about 24 hours or more.

9. A dosage regimen for administering tramadol to a patient for the treatment of pain comprising administering: about 175 mg to about 225 mg of tramadol in a controlled release dosage form once-a-day for about 4 to about 10 days; then about 275 mg to about 325 mg of tramadol in a controlled release dosage form once-a-day for at least 1 day and optionally thereafter.

10. The dosage regimen of claim 9 wherein the controlled release dosage forms are each oral dosage forms.

11. The dosage regimen of claim 10 wherein the tramadol is present in each oral dosage form in the form of tramadol hydrochloride.

12. The dosage regimen of claim 11 wherein each oral dosage form provides an in vitro release of tramadol hydrochloride of about 24 hours or more.

13. The dosage regimen of claim 9 comprising administering about 275 mg to about 325 mg of tramadol in a controlled release dosage form once-a-day for at least 6 days and optionally thereafter.

14. A dosage regimen for administering tramadol to a patient for the treatment of pain comprising administering: about 200 mg of tramadol in a controlled release dosage form once-a-day for days 1 through 7; then about 300 mg of tramadol in a controlled release dosage form once-a-day for at least 1 day and optionally thereafter.

15. The dosage regimen of claim 14 wherein the controlled release dosage forms are each oral dosage forms.

16. The dosage regimen of claim 15 wherein the tramadol is present in each oral dosage form in the form of tramadol hydrochloride.

17. The dosage regimen of claim 16 wherein each oral dosage form provides an in vitro release of tramadol hydrochloride of about 24 hours or more.

18. The dosage regimen of claim 14 comprising administering about 300 mg of tramadol in a controlled release dosage form once-a-day for at least 7 days and optionally thereafter.

19. A kit for the administration of a dosage regimen of tramadol comprising: instructions to administer the following amounts of tramadol in controlled release oral dosage forms according to the following dosage regimen: 100 mg of tramadol once-a-day on days 1 through 7; 200 mg of tramadol once-a-day on about days 8 through 14; and 300 mg of tramadol once-a-day on about days 15 through 21, and optionally thereafter; and a sufficient quantity of controlled release oral dosage forms of tramadol to administer tramadol according to the dosage regimen.

20. A kit for the administration of a dosage regimen of tramadol comprising: instructions to administer the following amounts of tramadol in controlled release oral dosage forms according to the following dosage regimen: 200 mg of tramadol once-a-day on days 1 through 7; and 300 mg of tramadol once-a-day on about days 8 through 14, and optionally thereafter; and a sufficient quantity of controlled release oral dosage forms of tramadol to administer tramadol according to the dosage regimen.

* * * * *